United States Patent
Cen et al.

(10) Patent No.: US 12,006,276 B2
(45) Date of Patent: Jun. 11, 2024

(54) DIBROMOBENZYL DERIVATIVE, STEREOISOMER OR SALT THEREOF, AND PREPARATION METHOD AND APPLICATION OF DIBROMOBENZYL DERIVATIVE

(71) Applicant: CHENGDU SHIBEIKANG BIOMEDICAL TECHNOLOGY CO., LTD., Sichuan (CN)

(72) Inventors: Guodong Cen, Sichuan (CN); Maoting Yang, Sichuan (CN); Shaojun Tan, Sichuan (CN)

(73) Assignee: CHENGDU SHIBEIKANG BIOMEDICAL TECHNOLOGY CO., LTD., Sichuan (CN)

( * ) Notice: Subject to any disclaimer, the term of this patent is extended or adjusted under 35 U.S.C. 154(b) by 161 days.

(21) Appl. No.: 17/629,617

(22) PCT Filed: Mar. 25, 2020

(86) PCT No.: PCT/CN2020/081092
§ 371 (c)(1),
(2) Date: Jan. 24, 2022

(87) PCT Pub. No.: WO2021/012698
PCT Pub. Date: Jan. 28, 2021

(65) Prior Publication Data
US 2022/0251024 A1 Aug. 11, 2022

(30) Foreign Application Priority Data

Jul. 24, 2019 (CN) .......................... 201910671508.7

(51) Int. Cl.
| C07C 215/44 | (2006.01) |
| A61K 31/137 | (2006.01) |
| C07C 209/52 | (2006.01) |
| C07C 213/02 | (2006.01) |
| C07C 249/02 | (2006.01) |

(52) U.S. Cl.
CPC .......... C07C 213/02 (2013.01); C07C 209/52 (2013.01); C07C 249/02 (2013.01)

(58) Field of Classification Search
CPC . C07C 2601/08; C07C 215/44; C07C 211/52; C07C 209/52; C07C 249/02; A61K 31/137
See application file for complete search history.

(56) References Cited

U.S. PATENT DOCUMENTS 3,536,713 A   10/1970   Keck et al.

FOREIGN PATENT DOCUMENTS

| CN | 101544572 A | 9/2009 |
| CN | 105693764 A | 6/2016 |

OTHER PUBLICATIONS

Chemical Catalog (Feb. 26, 2016). (Year: 2016).*
Kumar et al. Salt Selection in Drug Development. Pharmaceutical Technology, vol. 32, No. 3. (Year: 2008).*
"STN Retrieve Records", STN (reg database),Mar. 1, 2016, RN : 1874745-62-6 et al. 13 compounds. 1-8.

* cited by examiner

*Primary Examiner* — Sikarl A Witherspoon
(74) *Attorney, Agent, or Firm* — NKL Law; Allen Xue

(57) ABSTRACT

A dibromobenzyl derivative with a structure shown as formula I, a stereoisomer or a pharmaceutically acceptable salt thereof and a preparation method and an application of the dibromobenzyl derivative are provided. The dibromobenzyl derivative or the stereoisomer thereof is superior in in-vivo pharmacokinetic stability and drug efficacy, and capable of being used for preparing respiratory drugs, in particular the apophlegmatic drugs.

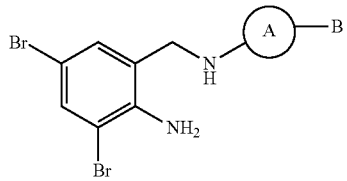

Formula I

9 Claims, No Drawings

DIBROMOBENZYL DERIVATIVE, STEREOISOMER OR SALT THEREOF, AND PREPARATION METHOD AND APPLICATION OF DIBROMOBENZYL DERIVATIVE

TECHNICAL FIELD

The present invention relates to the field of pharmaceutical chemistry, in particular to a dibromobenzyl derivative, a stereoisomer or a pharmaceutically acceptable salt thereof, and a preparation method and an application of the dibromobenzyl derivative.

BACKGROUND

As an in-vivo bromhexine metabolite, ambroxol effectively improves the ventilation function and relieving dyspnea by promoting the secretion of pulmonary surfactant and airway surface liquid, breaking down the mucopolysaccharide-protein fiber in phlegm, promoting the mucolysis, significantly reducing the viscosity of phlegm, enhancing the bronchial mucociliary transport and promoting the phlegm discharge. The ambroxol has become a commonly used apophlegmatic drug with apophlegmatic effect, toxicity and resistance significantly improved from the bromhexine. In 1984, the ambroxol was used clinically in the form of hydrochloride and applicable to acute/chronic pulmonary diseases with abnormal phlegm secretion and poor expectoration function, such as expectorant treatment of acute exacerbation of chronic bronchitis, asthmatic bronchitis and bronchial asthma, preventive treatment of post-operative pulmonary complications and treatment of infant respiratory distress syndrome (IRDS) in premature infants and newborns.

The ambroxol hydrochloride has been marketed in China in the form of lyophilized powder for injection as well as small- and large-volume parenteral injections. As a conventional apophlegmatic drug, it has been available in the global market for more than 30 years with clinically qualified effectiveness. However, the hydroxyl group in the cyclohexane combines with the glucuronic acid in human body and further deactivates the ambroxol. Therefore, the ambroxol hydrochloride has poor in-vivo metabolic stability and needs to be administered 2 or 3 times a day, and unsatisfactory expectorant effect is often reported clinically. Therefore, it is urgent to develop a novel apophlegmatic drug with improved effectiveness and in-vivo stability.

SUMMARY

In order to solve the above-mentioned technical problems, the objective of the present invention is to provide a dibromobenzyl derivative, a stereoisomer or a pharmaceutically acceptable salt thereof and a preparation method and an application of the dibromobenzyl derivative. The dibromobenzyl derivative and the stereoisomer have good in-vivo pharmacokinetic stability and enhanced drug efficacy by means of structural modification of cyclohexane in ambroxol, and is applicable to preparation of a respiratory drug, in particular an apophlegmatic drug.

In order to achieve the above objectives, the technical solution adopted in the present invention is as follows:

A dibromobenzyl derivative with a structure shown as formula I, a stereoisomer or a pharmaceutically acceptable salt thereof,

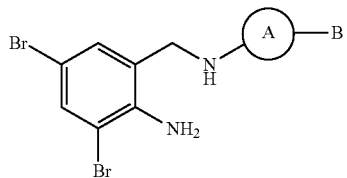

Formula I where, A is three-membered cycloalkane, four-membered cycloalkane, five-membered cycloalkane, seven-membered cycloalkane or adamantane; and B is hydrogen, alkane, hydroxyl group, halogen or halogenated alkane.

Further, the A is the four-membered cycloalkane, the five-membered cycloalkane or the adamantane.

Further, the A is the five-membered cycloalkane or the adamantane; the B is the hydrogen, C1-C5 alkane, the hydroxyl group, the halogen or the halogenated alkane.

Further, the B is C1-C5 alkane, the hydroxyl group, the halogen or the halogenated alkane.

Particularly, the structure of the dibromobenzyl derivative or the stereoisomer thereof is selected from any one of the group consisting of:

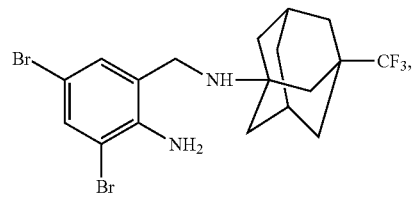

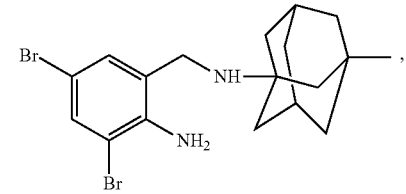

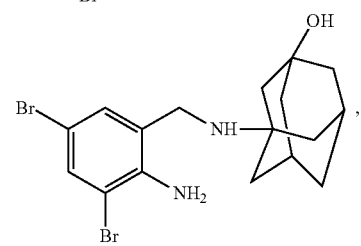

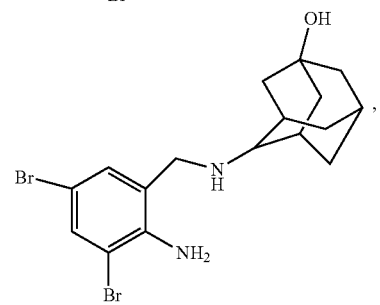

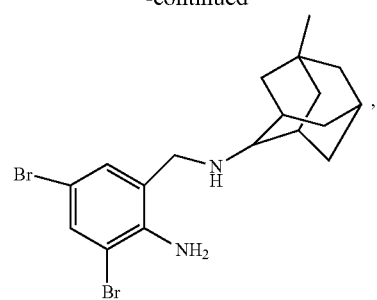
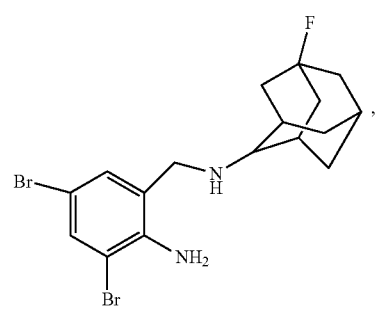
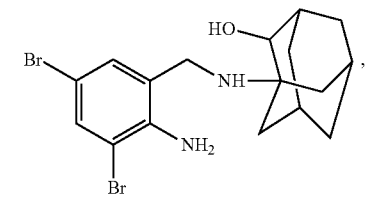
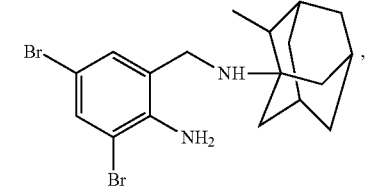
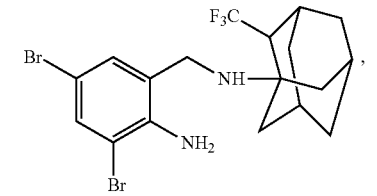
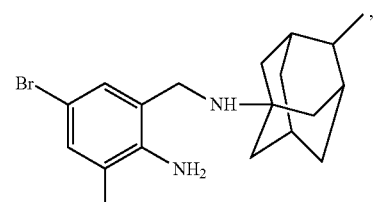
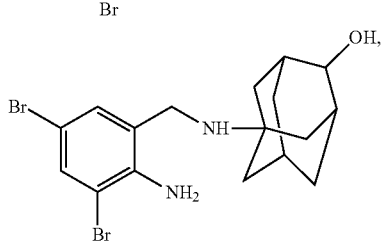
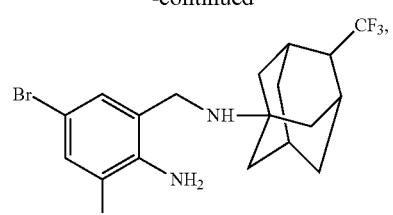
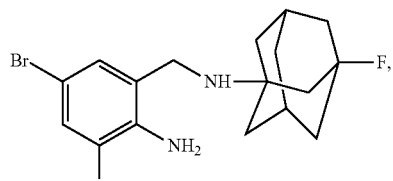
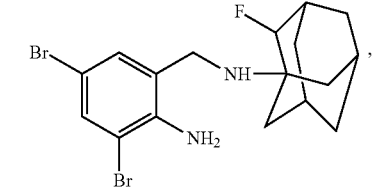
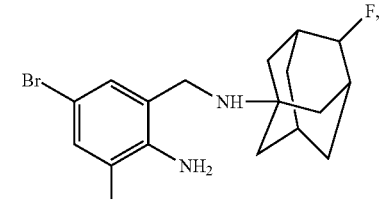
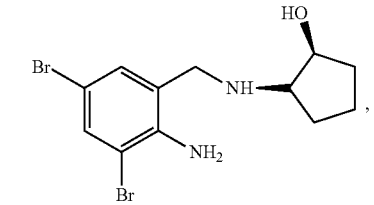
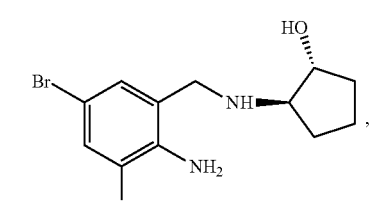
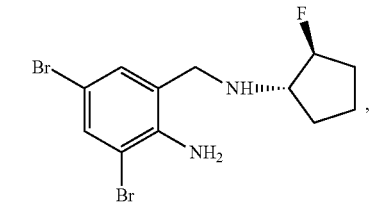
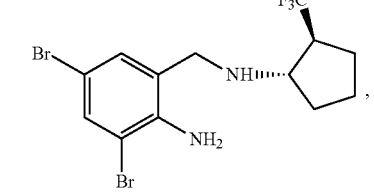

-continued

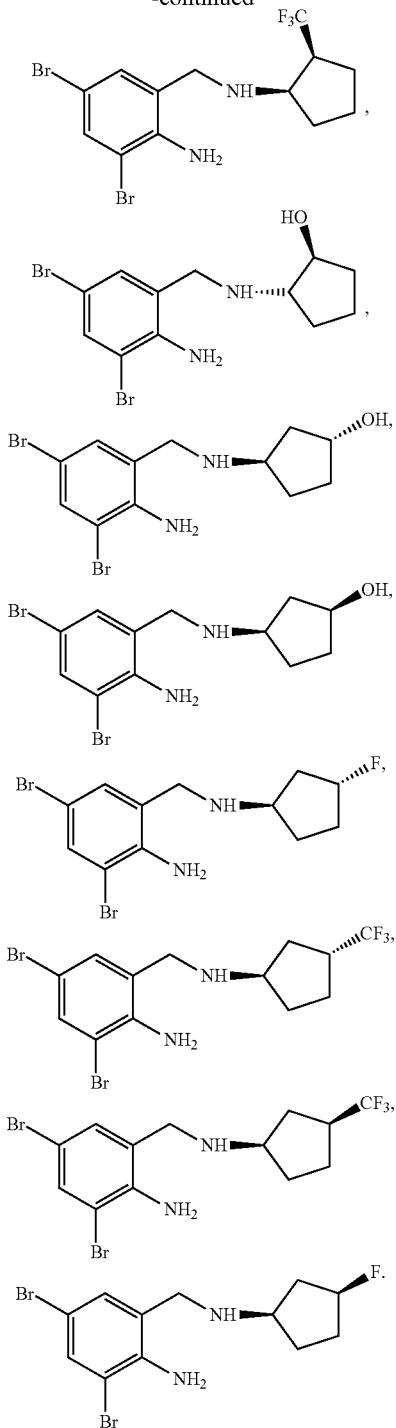

Particularly, the dibromobenzyl derivative is selected from the group consisting of:
3-((2-amino-3,5-dibromobenzyl)amino)adamantane-1-ol,
4-((2-amino-3,5-dibromobenzyl)amino)adamantane-1-ol,
(1R,2R)-2-((2-amino-3,5-dibromobenzyl)amino)-cyclopentanol,
(2-amino-3,5-dibromobenzyl)-3-methyl-adamantane-1-amine,
(1R,2S)-2-trifluoromethyl-((2-amino-3,5-dibromobenzyl)amino)-cyclopentane,
(2-amino-3,5-dibromobenzyl)-2-fluoro-adamantane-1-amine,
(1R,3R)-3-((2-amino-3,5-dibromobenzyl)amino)-cyclopentanol,
1-((2-amino-3,5-dibromobenzyl)amino)adamantane-2-ol and
(1S,2R)-2-((2-amino-3,5-dibromobenzyl)amino)-cyclopentanol.

Preferably, the dibromobenzyl derivative is selected from the group consisting of:
3-((2-amino-3,5-dibromobenzyl)amino)adamantane-1-ol;
4-((2-amino-3,5-dibromobenzyl)amino)adamantane-1-ol
(1R,2R)-2-((2-amino-3,5-dibromobenzyl)amino)-cyclopentanol.

Further, the pharmaceutically acceptable salt is formed by the dibromobenzyl derivative and an acid. Particularly, the acid is acetate, bisulfate, ascorbate, benzoate, benzene sulfonate, citrate, fumarate, hydrochloride, hydrobromide, maleate, mesylate, nitrate, oxalate, phosphate, succinate or sulfate.

A method for preparing the dibromobenzyl derivative with the structure shown as formula I according to the present invention, which includes the following steps: allow amino-A-B to react with 2-amino-3,5-dibromobenzaldehyde, and add a reducing agent for reduction after the reaction is complete, with a reaction formula as shown below:

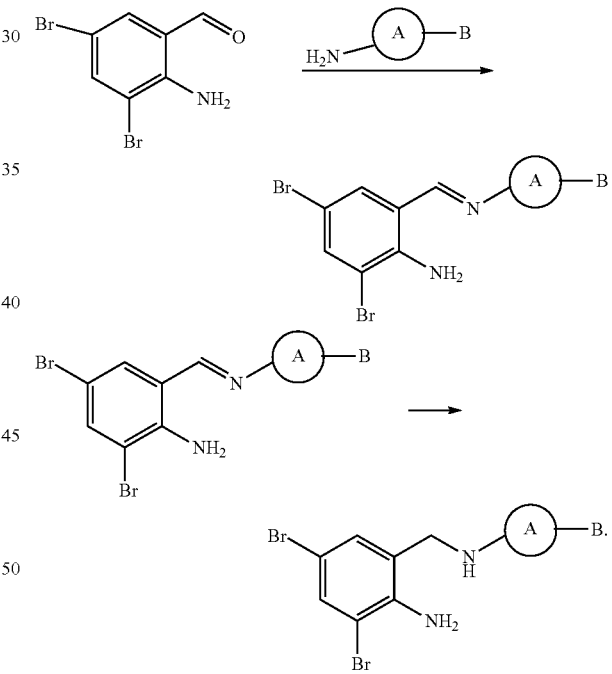

The reducing agent is sodium borohydride or potassium borohydride.

Preferably, the preparation method includes the following steps: add the amino-A-B, the 2-amino-3,5-dibromobenzaldehyde and 100 mL of tetrahydrofuran to a reaction flask, run overnight reaction by refluxing until the APIs basically disappear, cool to a room temperature, add the sodium borohydride or the potassium borohydride to react for 20-40 hrs, add 200-300 mL of water, extract with 300 mL of ethyl acetate, and produce a compound of the dibromobenzyl derivative or the stereoisomer thereof by vacuum concentration; and on this basis, wash the compound obtained with 100 mL of saturated sodium chloride, acidify it with an acid, and produce corresponding compound salt by vacuum concentration.

Also provided in the present invention is an application of the dibromobenzyl derivative, the stereoisomer or the pharmaceutically acceptable salt thereof in preparation of a drug for preventing and treating respiratory diseases.

Further provided in the present invention is an application of the dibromobenzyl derivative, the stereoisomer or the pharmaceutically acceptable salt thereof in preparation of an apophlegmatic drug.

Further provided in the present invention is a pharmaceutical composition, which includes the dibromobenzyl derivative, the stereoisomer or the pharmaceutically acceptable salt thereof and a pharmaceutically acceptable carrier.

The "pharmaceutically acceptable carrier" refers to a diluent, adjuvant, excipient or medium administered with a therapeutic agent, and suitable for being exposed to human tissue and/or other animal tissues within the extent of reasonable medical judgment without excessive toxicity, irritation, anaphylaxis or other problems or complications corresponding to a reasonable benefit/risk ratio.

Compared with the prior art, the present invention has the following beneficial effects:

A structure of the cyclohexane in the ambroxol is creatively modified in the present invention to obtain the dibromobenzyl derivative and the stereoisomer thereof according to the present invention. The inventor has surprisingly found that the dibromobenzyl derivative and the stereoisomer thereof according to the present invention are superior in efficacy and bioavailability to ambroxol hydrochloride, and have excellent expectorant effect according to capillary expectoration test in rats and phenol red expectoration test in mice. Compared with the positive control group of ambroxol hydrochloride, they have significantly improved efficacy, longer pharmacokinetic half-life and remarkable progress.

DESCRIPTION OF THE PREFERRED EMBODIMENTS

The present invention will be further described in detail in combination with embodiments. The method provided by the present invention includes but not limited to the following embodiments.

In the following examples, the specific structures of dibromobenzyl derivative and stereoisomer thereof are determined by mass spectrometry (MS) or 1H nuclear magnetic resonance (1HNMR). Wherein, the 1HNMR shift (δ) is expressed in parts per million (ppm); and 1HNMR measurement is realized by BrukerAVANCE-400 NMR spectrometer. All raw materials used in the embodiments of the present invention are commercially available.

Example 1

This example discloses a preparation method of a compound 1: 3-((2-amino-3,5-dibromobenzyl)amino)adamantane-1-ol, with a structure shown as follows:

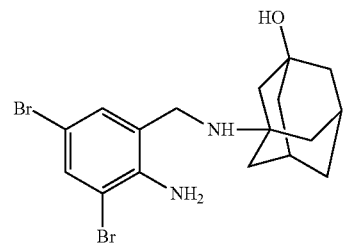 [SMILES: Nc1c(Br)cc(Br)cc1CNC12CC3CC(CC(O)(C3)C1)C2]

Add 3 g (0.018 mol) of 3-amino-1-adamantanol, 10 g (0.036 mol) of 2-amino-3,5-dibromobenzaldehyde and 100 mL of tetrahydrofuran (THF) to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, and produce the compound 1 with a total weight of 6.60 g, an HPLC-based purity of 98.70% and a yield of 86% by vacuum concentration.

MS m/z (ES): 429.01

1H NMR (400 MHz, $D_2O$) δ 7.81 (d, 1H), 7.21 (d, 1H), 3.76 (s, 2H), 1.76 (s, 2H), 1.68-1.66 (m, 6H), 1.46-1.55 (m, 4H), 1.34-1.38 (m, 4H).

Example 2

This example discloses a preparation method of a compound 2: 3-((2-amino-3,5-dibromobenzyl) amino) adamantane-1-ol hydrochloride, with a structure shown as follows:

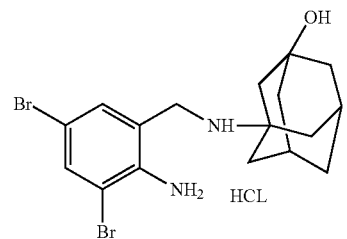 [SMILES: Nc1c(Br)cc(Br)cc1CNC12CC3CC(CC(O)(C3)C1)C2]

Prepare the compound 1 according to the method of Example 1, wash 0.018 mol of the compound 1 with 100 mL of saturated sodium chloride, acidify with hydrochloric acid, and produce the dry compound 2 with a total weight of 7.06 g, an HPLC-based purity of 98.65% and a yield of 85% by vacuum concentration.

MS m/z (ES): 429.02

1H NMR (400 MHz, $D_2O$) δ 7.80 (d, 1H), 7.22 (d, 1H), 3.76 (s, 2H), 1.77 (s, 2H), 1.68-1.67 (m, 6H), 1.46-1.56 (m, 4H), 1.34-1.38 (m, 4H).

Example 3

This example discloses a preparation method of a compound 3: (1R,2R)-2-((2-amino-3,5-dibromobenzyl)amino)-cyclopentanol, with a structure shown as follows:

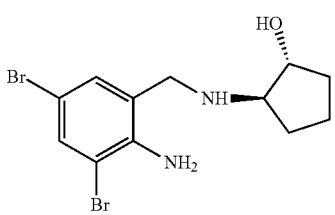 [SMILES: Nc1c(Br)cc(Br)cc1CN[C@@H]1CCC[C@H]1O]

Add 3 g (0.029 mol) of trans-(1R,2R)-2-amino cyclopentanol, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, and produce the compound 3 with a total weight of 8.90 g, an HPLC-based purity of 98.76% and a yield of 86% by vacuum concentration.

MS m/z (ES): 362.95

1H NMR (400 MHz, D$_2$O) δ7.81 (d, 1H), 7.28 (d, 1H), 3.45 (s, 2H), 4.22 (m, 1H), 3.59 (m, 1H), 2.09-2.34 (m, 2H), 1.53-1.72 (m, 4H).

Example 4

This example discloses a preparation method of a compound 4: (1R,2R)-2-((2-amino-3,5-dibromobenzyl)amino)-cyclopentanol bisulfate, with a structure shown as follows:

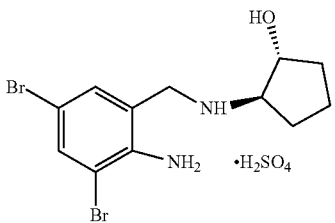

Prepare the compound 3 according to the method of Example 3, wash 0.029 mol of the compound 3 with 100 mL of saturated sodium chloride, acidify with sulfuric acid, and produce the dry compound 4 with a total weight of 10.60 g, an HPLC-based purity of 98.65% and a yield of 80% by vacuum concentration.

MS m/z (ES): 362.97

1H NMR (400 MHz, D$_2$O) δ7.82 (d, 1H), 7.27 (d, 1H), 3.45 (s, 2H), 4.23 (m, 1H), 3.59 (m, 1H), 2.09-2.33 (m, 2H), 1.53-1.73 (m, 4H).

Example 5

This example discloses a preparation method of a compound 5: (2-amino-3,5-dibromobenzyl)-3-methyl-adamantane-1-amine, with a structure shown as follows:

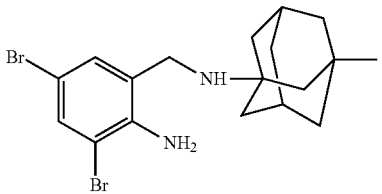 [SMILES: CC12CC3CC(C1)CC(NCc1cc(Br)cc(Br)c1N)(C3)C2]

Add 3 g (0.018 mol) of 3-methyl-1-amantadine, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, wash with 100 mL of saturated sodium chloride to form an organic phase, and produce the dry compound 5 with a total weight of 6.36 g, an HPLC-based purity of 98.75% and a yield of 83% by vacuum concentration.

MS m/z (ES): 427.03[M+1]

1H NMR (400 MHz, D$_2$O) δ 7.82 (d, 1H), 7.25 (d, 1H), 3.78 (s, 2H), 1.78 (s, 2H), 1.68-1.69 (m, 6H), 1.45-1.57 (m, 4H), 1.34-1.38 (m, 2H), 1.12 (s, 3H).

Example 6

This example discloses a preparation method of a compound 6: (2-amino-3,5-dibromobenzyl)-3-trifluoromethyl-adamantane-1-amine, with a structure shown as follows:

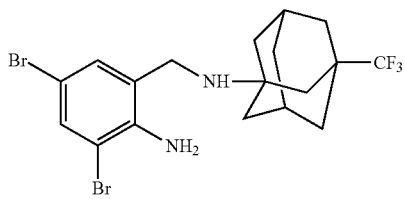 [SMILES: Nc1c(Br)cc(Br)cc1CNC12CC3CC(C1)CC(C(F)(F)F)(C3)C2]

Add 3 g (0.0136 mol) of 3-trifluoromethyl-1-amantadine, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, wash with 100 mL of saturated sodium chloride to form an organic phase, and produce the dry compound 6 with a total weight of 5.74 g, an HPLC-based purity of 99.65% and a yield of 88% by vacuum concentration.

MS m/z (ES): 481.00[M+1]

1H NMR (400 MHz, D$_2$O) δ 7.89 (d, 1H), 7.23 (d, 1H), 3.79 (s, 2H), 1.78 (s, 2H), 1.55-1.69 (m, 6H), 1.45-1.50 (m, 4H), 1.34-1.38 (m, 2H).

Example 7

This example discloses a preparation method of a compound 7: (1R,2S)-2-trifluoromethyl-((2-amino-3,5-dibromobenzyl)amino)-cyclopentane, with a structure shown as follows:

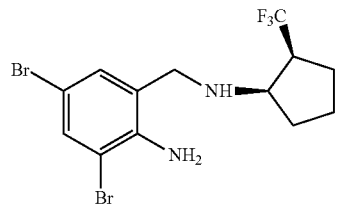 [SMILES: Nc1c(Br)cc(Br)cc1CN[C@@H]1CCC[C@@H]1C(F)(F)F]

Add 3 g (0.0196 mol) of (1R,2S)-2-trifluoromethyl-cyclopentylamine, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, wash with 100 mL of saturated sodium chloride to form an organic phase, and produce the dry compound 7 with a total weight of 7.08 g, an HPLC-based purity of 99.56% and a yield of 90% by vacuum concentration.

MS m/z (ES): 414.96 [M+1]

1H NMR (400 MHz, $D_2O$) δ7.88 (d, 1H), 7.24 (d, 1H), 3.45 (s, 2H), 3.57 (m, 1H), 2.09-2.23 (m, 2H), 1.53-1.63 (m, 4H).

Example 8

This example discloses a preparation method of a compound 8: (2-amino-3,5-dibromobenzyl)-2-fluoro-adamantane-1-amine, with a structure shown as follows:

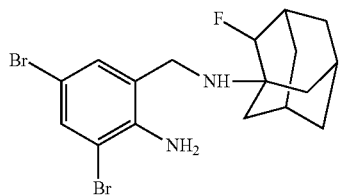 [SMILES: Nc1c(Br)cc(Br)cc1CNC12CC3CC(CC(C3)C1F)C2]

Add 3 g (0.018 mol) of 2-fluoro-1-amantadine, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, wash with 100 mL of saturated sodium chloride to form an organic phase, and produce the dry compound 8 with a total weight of 7.00 g, an HPLC-based purity of 99.36% and a yield of 92% by vacuum concentration.

MS m/z (ES): 431.01 [M+1]

1H NMR (400 MHz, $D_2O$) δ 7.79 (d, 1H), 7.33 (d, 1H), 3.77 (s, 2H), 3.02 (s, 1H), 1.55-1.69 (m, 6H), 1.42-1.50 (m, 4H), 1.24-1.34 (m, 3H).

Example 9

This example discloses a preparation method of a compound 9: (1R,3R)-3-((2-amino-3,5-dibromobenzyl)amino)-cyclopentanol, with a structure shown as follows:

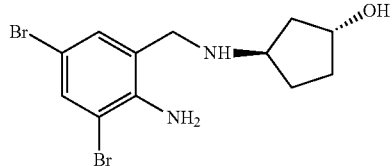 [SMILES: Nc1c(Br)cc(Br)cc1CN[C@@H]1CC[C@@H](O)C1]

Add 3 g (0.029 mol) of (1R,3R)-3-amino cyclopentanol, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, wash with 100 mL of saturated sodium chloride to form an organic phase, and produce the dry compound 9 with a total weight of 8.75 g, an HPLC-based purity of 98.45% and a yield of 83% by vacuum concentration.

MS m/z (ES): 361.97 [M+1]

1H NMR (400 MHz, $D_2O$) δ7.80 (d, 1H), 7.25 (d, 1H), 3.46 (s, 2H), 4.20 (m, 1H), 3.57 (m, 1H), 2.09-2.13 (m, 2H), 1.63-1.73 (m, 4H).

Example 10

This example discloses a preparation method of a compound 10: 1-((2-amino-3,5-dibromobenzyl)amino)adamantane-2-ol, with a structure shown as follows:

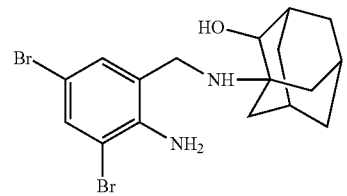 [SMILES: Nc1c(Br)cc(Br)cc1CNC12CC3CC(CC(C3)C1O)C2]

Add 3 g (0.018 mol) of 2-amino-1-adamantanol, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, wash with 100 mL of saturated sodium chloride, and produce the dry compound 10 with a total weight of 6.60 g, an HPLC-based purity of 97.65% and a yield of 86% by vacuum concentration.

MS m/z (ES): 429.01[M+1]

1H NMR (400 MHz, $D_2O$) δ 7.81 (d, 1H), 7.24 (d, 1H), 3.77 (s, 2H), 3.50 (m, 1H) 1.77 (m, 2H), 1.68-1.69 (m, 6H), 1.46-1.58 (m, 4H), 1.35-1.38 (m, 3H).

Example 11

This example discloses a preparation method of a compound 11: (1S,2R)-2-((2-amino-3,5-dibromobenzyl)amino)-cyclopentanol, with a structure shown as follows:

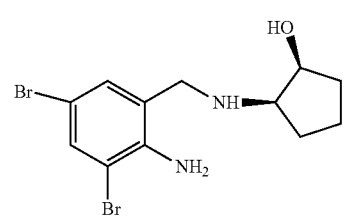 [SMILES: Nc1c(Br)cc(Br)cc1CN[C@@H]1CCC[C@@H]1O]

Add 3 g (0.029 mol) of (1S,2R)-2-amino cyclopentanol, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, wash with 100 mL of saturated sodium chloride, and produce the dry compound 11 with a total weight of 8.74 g, an HPLC-based purity of 97.45% and a yield of 82% by vacuum concentration.

MS m/z (ES): 361.97[M+1]

1H NMR (400 MHz, D$_2$O) δ7.84 (d, 1H), 7.23 (d, 1H), 3.45 (s, 2H), 4.20 (m, 1H), 3.59 (m, 1H), 2.09-2.14 (m, 2H), 1.63-1.78 (m, 4H).

Example 12

This example discloses a preparation method of a compound 12: 4-((2-amino-3,5-dibromobenzyl)amino)adamantane-1-ol, with a structure shown as follows:

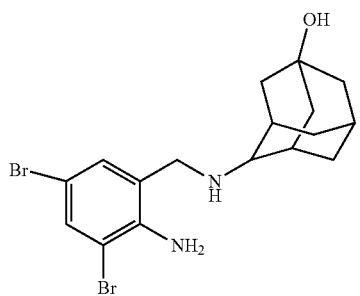 [SMILES: Nc1c(Br)cc(Br)cc1CNC1C2CC3CC1CC(O)(C3)C2]

Add 3 g (0.018 mol) of 4-amino-1-adamantanol, 10 g (0.036 mol) of 2-amino-3,5-dibromobenzaldehyde and 100 mL of THF to a reaction flask, run overnight reaction by refluxing until the APIs basically disappear under TCL monitoring, cool to a room temperature, add 2.5 g (0.066 mol) of sodium borohydride to react for 24 hrs, add about 250 mL of water, extract with 300 mL of ethyl acetate, and produce the compound 12 with a total weight of 6.10 g, an HPLC-based purity of 97.80% and a yield of 80% by vacuum concentration.

MS m/z (ES): 429.01

1H NMR (400 MHz, D$_2$O) δ 7.83 (d, 1H), 7.20 (d, 1H), 4.50 (s, 1H), 3.76 (s, 2H), 1.75 (s, 2H), 1.60-1.66 (m, 6H), 1.46-1.54 (m, 4H), 1.34-1.39 (m, 4H).

Example 13

This example discloses a preparation method of a compound 13: 4-((2-amino-3,5-dibromobenzyl)amino)adamantane-1-ol hydrochloride, with a structure shown as follows:

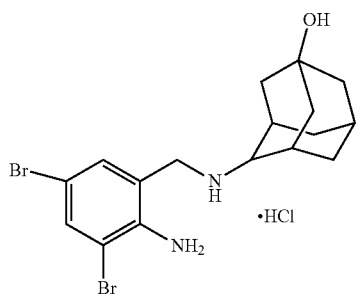 [SMILES: Nc1c(Br)cc(Br)cc1CNC1C2CC3CC1CC(O)(C3)C2 ; Cl]

According to the method for preparing the compound 12, wash 0.020 mol of the compound 12 with 100 mL of saturated sodium chloride, acidify with hydrochloric acid, and produce the dry compound 13 with a total weight of 7.06 g, an HPLC-based purity of 97.60% and a yield of 78% by vacuum concentration.

MS m/z (ES): 429.02

1H NMR (400 MHz, D$_2$O) δ 7.80 (d, 1H), 7.22 (d, 1H), 4.49 (s, 1H), 3.76 (s, 2H), 1.77 (s, 2H), 1.68-1.67 (m, 6H), 1.46-1.56 (m, 4H), 1.34-1.38 (m, 4H).

In order to test properties and purposes of the compounds of the present invention, the following test examples are further conducted with the compounds produced in the above-mentioned embodiments, as shown below:

Test Example 1

Capillary Expectoration Test in Rats

The female and male SD rats with body weights ranging from 180 g to 220 g are randomLy allocated into 9 groups (n=10 rats). Before measuring the length of phlegm expelled, the rats are prohibited to eat but allowed to drink for 12 hrs, and then administrated via tail veins with corresponding products (dissolved in normal saline to adjust pH) or normal saline. After 30 mins, urethane saline solution (1 g/kg) is injected intraperitoneally for anesthesia, and the rats are fixed in a supine position for neck incision and trachea separation. A puncture is made between the superior and middle cartilage rings on the inferior margin of thyroid cartilage with an injection needle, and a capillary tube (with an inner diameter of 0.8 mm and a length of 10 cm) is inserted into the trachea towards the heart. The angle between the capillary tube and the trachea is adjusted to collect the phlegm, and the expectoration effect is evaluated based on a total length (mm) of the phlegm in the capillary tube. The 90-min lengths of phlegm expelled are recorded for statistical analysis by groups, as shown in Table 1.

TABLE 1

Effect on length of phlegm expelled in rats by capillary expectoration test ($\bar{x} \pm s$)

| Group | Test product | Dose (mg/kg) | Number of animals | 90-min length of phlegm expelled (mm) |
|---|---|---|---|---|
| Control Group | Normal saline | — | 10 | 23.9 ± 4.60 |
| Example 1 group | Example 1 compound | 15 | 10 | 39.9 ± 5.35**▲ |
| Example 3 group | Example 3 compound | 15 | 10 | 37.8 ± 6.45**▲ |
| Example 5 group | Example 5 compound | 15 | 10 | 36.9 ± 5.45**▲ |
| Example 6 group | Example 6 compound | 15 | 10 | 35.2 ± 4.79*▲ |
| Example 7 group | Example 7 compound | 15 | 10 | 31.8 ± 5.73* |
| Example 8 group | Example 8 compound | 15 | 10 | 35.8 ± 5.98*▲ |
| Example 12 group | Example 12 compound | 15 | 10 | 39.8 ± 5.31**▲ |
| Ambroxol hydrochloride group | Ambroxol hydrochloride | 15 | 10 | 29.9 ± 4.96* |

Note:
Compared with the control group: *$P < 0.05$, **$P < 0.01$; Compared with the ambroxol hydrochloride group, ▲$P < 0.05$;

According to Table 1: compared with the control group, all the test samples significantly increase the length of phlegm in rats, and the differences are statistically significant ($P<0.01$ or $P<0.05$); and compared with the ambroxol hydrochloride group, the compounds in the Examples 1, 3, 5, 6, 8 and 12 groups significantly increase the excretory amounts of phenol red from trachea of mice (▲$P<0.05$) and are remarkably superior to the ambroxol hydrochloride, in particular the compounds in the Examples 1, 3, 5 and 12.

Test Example 2

Phenol Red Expectoration Test in Mice

Methods: Seventy-two female and male mice are randomLy allocated into a control group (normal saline), an Example 1 group (30 mg/kg, as free alkali), an Example 3 group (30 mg/kg, as free alkali), an Example 5 group (30 mg/kg, as free alkali), an Example 12 group (30 mg/kg, as free alkali) and an ambroxol hydrochloride group (30 mg/kg, as free alkali) (n=12 mice); These mice are administrated twice in successive via tail veins with corresponding products (dissolved in normal saline to adjust pH) or normal saline, and then receive 5% phenol red saline solution (0.5 g/kg) by hypodermic administration 15 mins after the last dose. After 30 mins, these mice are sacrificed, and a section of trachea from inferior thyroid cartilage to branch of trachea is cut off and placed in a test tube containing 1 mL of normal saline, shaken and soaked for 30 mins, and then centrifuged for 10 mins (at 3000 r/min) to obtain a supernatant, which is transferred to another tube, shaken well with 0.1 mL of 1M NaOH, and determined by means of a colorimetric method at a wavelength of 546 nm. The effects on excretory amounts of phenol red from trachea of mice among groups are analyzed and compared, and results are shown in Table 2:

TABLE 2

Effect on the excretory amounts of phenol red from trachea of mice ($\bar{x} \pm s$)

| Group | Test sample | Dose (mg/kg) | Number of animals (mouse) | Excretory amount of phenol red (OD value) |
|---|---|---|---|---|
| Control group | Normal saline | — | 12 | 0.098 ± 0.021 |
| Example 1 group | Example 1 compound | 30 | 12 | 0.220 ± 0.063*▲ |
| Example 3 group | Example 3 compound | 30 | 12 | 0.218 ± 0.052*▲ |
| Example 5 group | Example 5 compound | 30 | 12 | 0.201 ± 0.062*▲ |
| Example 12 group | Example 12 compound | 30 | 12 | 0.221 ± 0.059*▲ |
| Ambroxol hydrochloride group | Ambroxol hydrochloride | 30 | 12 | 0.131 ± 0.015* |

Note:
Compared with the control group: *P < 0.05; Compared with the ambroxol hydrochloride group, ▲P < 0.05;

According to Table 2: compared with the mice in the control group, the compounds in the Examples 1, 3, 5 and 12 groups and a ambroxol hydrochloride group significantly increase the excretory amounts of phenol red from trachea of mice (* p<0.05); and compared with the ambroxol hydrochloride group, the compounds in the Examples 1, 3, 5 and 12 groups significantly increase the excretory amounts of phenol red from trachea of mice (▲P<0.05) and are remarkably superior to the ambroxol hydrochloride.

The phenol red test is a classical animal-model expectoration test, the phenol red administrated intraperitoneally is partially excreted from the bronchus of mice, and the compounds in the Examples 1, 3, 5 and 12 groups significantly increase the excretory amounts of phenol red from trachea of mice (▲P<0.05) and are remarkably superior to the ambroxol hydrochloride. Therefore, the application of the compounds in respiratory drugs will result in improved efficacy, in particular the apophlegmatic drugs.

Test Example 3

Pharmacokinetics Test in Rats

Methods: Twenty-four female and male rats are randomLy allocated into an Example 1 compound group (10 mg/kg, as free alkali), an Example 3 compound group (10 mg/kg, as free alkali), an Example 12 compound group and an ambroxol hydrochloride group (10 mg/kg, as free alkali) (n=6); These rats are given corresponding products (dissolved in normal saline to adjust pH) intravenously. About 0.2 mL of blood samples is respectively collected from jugular veins before and 15.0 min, 30.0 min, 1.0 h, 2.0 h, 3.0 h, 4.0 h, 6.0 h, 8.0 h, 12.0 h and 24.0 h after the administration, and then centrifuged at a high speed (7800×g) for 15 min in a tube containing EDTA-K2. The separated plasma is stored at −15° C.~−35° C.

As shown in Table 3, test results are obtained by means of HPLC/MS/MS analysis, compartment model fitting for pharmacokinetic behaviors of the test compounds, and calculation of main pharmacokinetic parameters:

TABLE 3

Pharmacokinetic Parameters

| Group | Test sample | T1/2 (h) | CL (mL/h/kg) | MRT (h) | AUC AUC0-inf (h * ng/mL) |
|---|---|---|---|---|---|
| Example 1 group | Example 1 compound | 3.58 ± 0.45* | 2095 ± 105* | 2.58 ± 0.41* | 4472 ± 250* |
| Example 3 group | Example 3 compound | 3.12 ± 0.34* | 2860 ± 165* | 2.31 ± 0.36* | 3650 ± 180* |
| Example 12 group | Example 12 compound | 3.43 ± 0.35* | 2150 ± 145* | 2.65 ± 0.42* | 4490 ± 240* |
| Ambroxol hydrochloride group | Ambroxol hydrochloride | 1.98 ± 0.34 | 6051 ± 270 | 1.18 ± 0.20 | 1650 ± 71.9 |

Compared with the ambroxol hydrochloride group, *P < 0.05;

According to Table 3, the Example 1, Example 3 and Example 12 groups are significantly superior to the ambroxol hydrochloride group (*P<0.05) in half-life (T½), clearance (CL), mean retention time (MRT) and area under the curve (AUC), indicating that the in-vivo metabolic stability and pharmacokinetic properties of the compounds prepared in the embodiments of the present invention are remarkably improved from that of the ambroxol hydrochloride.

Only preferred embodiments of the present invention are described above, which should not be used for limiting the protection scope thereof. However, all modifications or polishing without any substantive meaning based on the main design idea and spirit of the present invention should fall into the protection scope of the present invention if they still solve the technical problem which is consistent with the one of the present invention.

The invention claimed is:

1. A dibromobenzyl derivative of Formula I, a stereoisomer, or a pharmaceutically acceptable salt thereof,

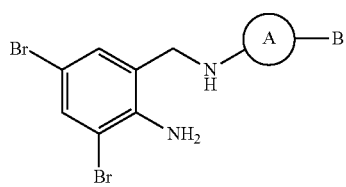

Formula I wherein, A is five-membered cycloalkane, or adamantane; and B is C1-C5 alkane, hydroxyl group, halogen, or halogenated alkane.

2. A dibromobenzyl derivative, a stereoisomer, or a pharmaceutically acceptable salt thereof, wherein the dibromobenzyl derivative is selected from the group consisting of:

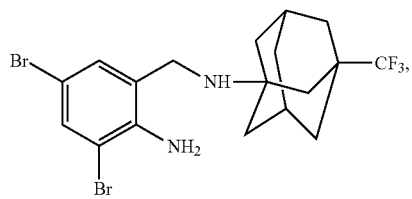

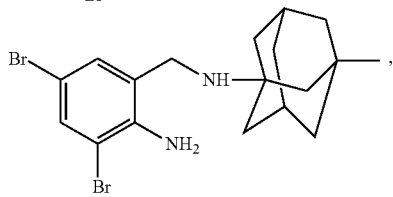

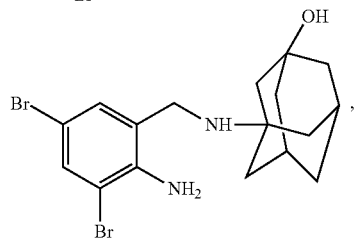

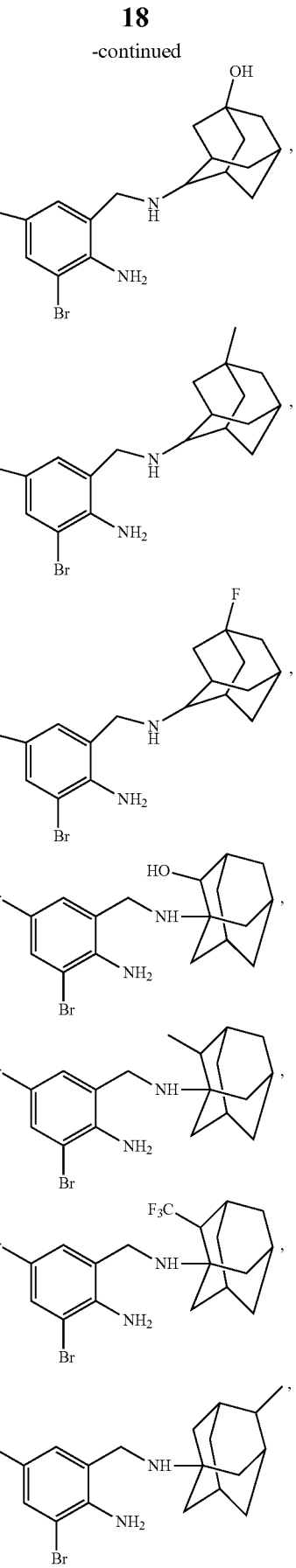

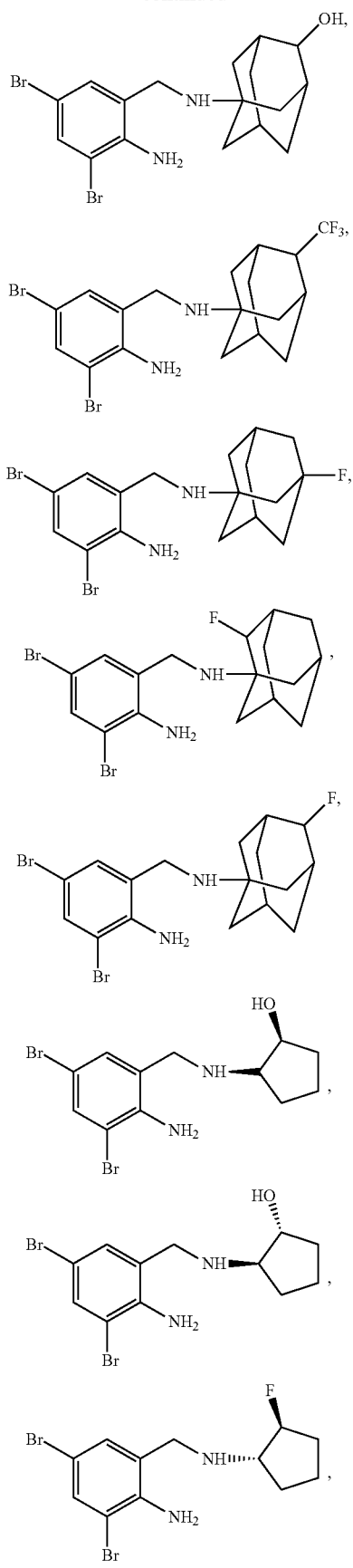
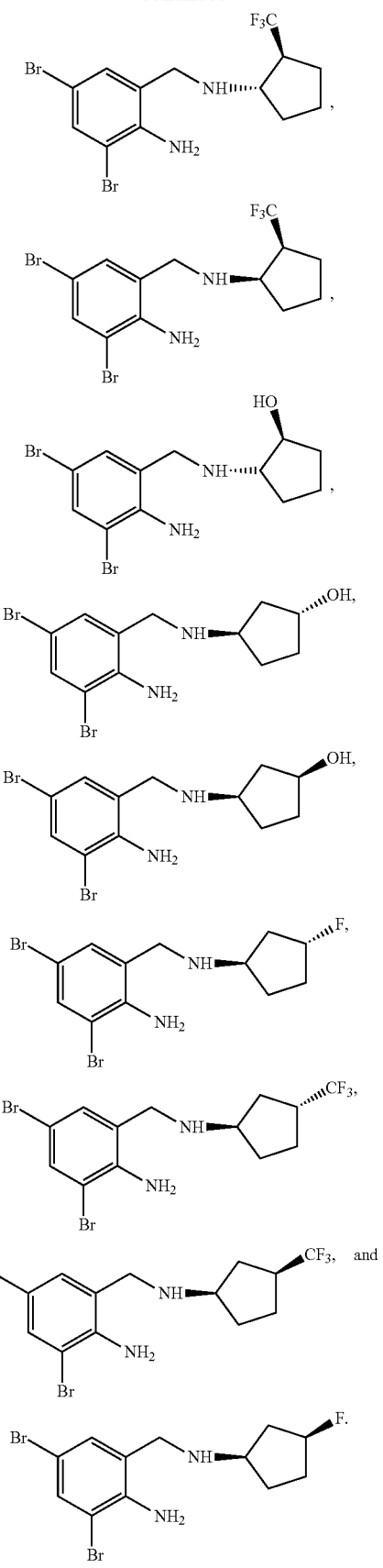

3. The dibromobenzyl derivative, the stereoisomer or the pharmaceutically acceptable salt thereof according to claim 2, wherein the dibromobenzyl derivative is selected from the group consisting of:
- 3-((2-amino-3,5-dibromobenzyl)amino)adamantane-1-ol,
- 4-((2-amino-3,5-dibromobenzyl)amino)adamantane-1-ol,
- (1R,2R)-2-((2-amino-3,5-dibromobenzyl)amino)-cyclopentanol,
- (2-amino-3,5-dibromobenzyl)-3-methyl-adamantane-1-amine,
- (1R,2S)-2-trifluoromethyl-((2-amino-3,5-dibromobenzyl)amino)-cyclopentane,
- (2-amino-3,5-dibromobenzyl)-2-fluoro-adamantane-1-amine,
- (1R,3R)-3-((2-amino-3,5-dibromobenzyl)amino)-cyclopentanol,
- 1-((2-amino-3,5-dibromobenzyl)amino)adamantane-2-ol, and
- (1S,2R)-2-((2-amino-3,5-dibromobenzyl)amino)-cyclopentanol.

4. The dibromobenzyl derivative, the stereoisomer or the pharmaceutically acceptable salt thereof according to claim 3, wherein the dibromobenzyl derivative is selected from the group consisting of:
- 3-((2-amino-3,5-dibromobenzyl)amino)adamantane-1-ol,
- 4-((2-amino-3,5-dibromobenzyl)amino)adamantane-1-ol, and
- (1R,2R)-2-((2-amino-3,5-dibromobenzyl)amino)-cyclopentanol.

5. The dibromobenzyl derivative, the stereoisomer or the pharmaceutically acceptable salt thereof according to claim 1, wherein the pharmaceutically acceptable salt is formed by the dibromobenzyl derivative and an acid.

6. A method for preparing the dibromobenzyl derivative of Formula I according to claim 1, comprising the following steps of:
reacting amino-A-B with 2-amino-3,5-dibromobenzaldehyde to form an intermediate of Formula II:

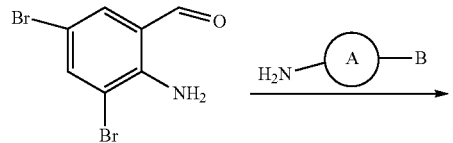

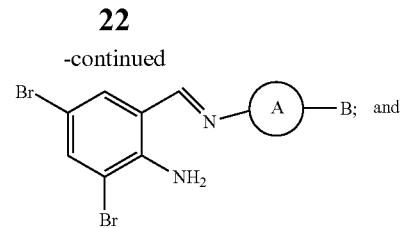

Formula II reacting a reducing agent with the intermediate of Formula II to obtain the dibromobenzyl derivative of Formula I:

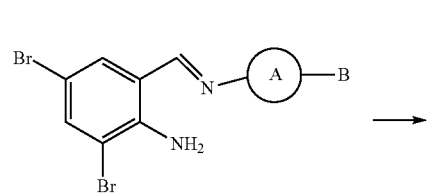

Formula II

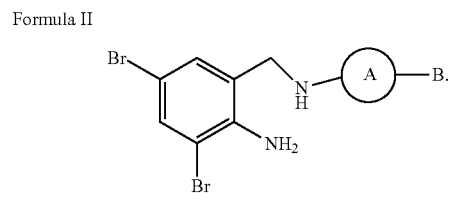

Formula I

7. The preparation method according to claim 6, wherein the reducing agent is sodium borohydride or potassium borohydride.

8. A pharmaceutical composition by comprising the dibromobenzyl derivative, the stereoisomer or the pharmaceutically acceptable salt thereof according to claim 1 and a pharmaceutically acceptable carrier.

9. A method for treating a respiratory disease, comprising administering the pharmaceutical composition according to claim 8 to a subject in need thereof.

* * * * *